United States Patent [19]
Takezawa et al.

[11] Patent Number: 5,985,539
[45] Date of Patent: Nov. 16, 1999

[54] METHOD OF RECONSTRUCTING ANIMAL ORGANS

[75] Inventors: Toshiaki Takezawa, Machida; Nobuo Hanai, Sagamihara, both of Japan

[73] Assignee: Kyowa Hakko Kogyo Co., Ltd., Tokyo, Japan

[21] Appl. No.: 09/112,211

[22] Filed: Jul. 9, 1998

[30] Foreign Application Priority Data

Jul. 10, 1997 [JP] Japan .................................. 9-185400
Sep. 30, 1997 [JP] Japan .................................. 9-265662

[51] Int. Cl.$^6$ ...................................................... A01N 1/02
[52] U.S. Cl. ............................................. 435/1.2; 435/1.1
[58] Field of Search ......................................... 435/1.1, 1.2

[56] References Cited

FOREIGN PATENT DOCUMENTS 0287896 of 1988 European Pat. Off. .

OTHER PUBLICATIONS

Vaananen et al., "Selective Isolation of Intact Peri–portal or PeriOvenous Hepatocytes by Anterograde or Retrograde Coallagenase Gradient Perfusion", Liver 3 (3) : 131–139 (1983).

J. Gerlach, et al "High Yield hepatocyte isolation from pig livers for investigation of hybrid liver support systems: influence of collagenase concentration and body weight" *Journal of Surgical Research,* vol. 62, 1996, pp. 85–89.

B.D. Foy et al: "Engineering organ perfusion protocols: NMR analysis of hepatocyte isolation from perfused rat liver" *Biotechnology and Bioengineering,* vol. 43, 1994, pp. 661–672.

M.E. Pueyo, et al: "A method for obtaining monodispersed cells from isolated porcine islets of Langerhans" *The International Journal of Artificial Organs,* vol. 18, No. 1, 1995.

M. Takahashi, et al: "Isolation and culture of human hepatocytes from resected liver tissue as a bioreactor for a hybrid artificial liver" *Artificial Organs,* vol. 17, No. 7, 1993, pp. 653–659.

A. K. Campbell, et al: "Maintenance of Viable Cells in an Organ Culture of Mature Rat Liver" *Experimental Cell Research* 68, (1971) pp. 33–42.

D. W. John, et al: "Effect of Aflatoxin B1 on Net Synthesis of Albumin, Fibrinogen, and α1 –Acid Clycoprotein by the Isolated Perfused Rat Liver" *Biochemical Pharmacology,* vol. 18, pp. 1135–1146; GB.

D. W. John, et al: "Influence of Actinomycin D and Puromycin on Net Synthesis of Plasma Albumin and Fibrinogen by the Isolated Perfused Rat Liver" *The Journal of Biological Chemistry,* vol. 241, No. 21, Issue of Nov. 10, pp. 4817–4824, (1966).

*Primary Examiner*—Sandra Saucier
*Attorney, Agent, or Firm*—Antonelli, Terry, Stout & Kraus

[57] ABSTRACT

The present invention relates to a method for reconstruction of animal organ which comprises perfusing a cell-dispersible solution to animal organ from vascular system and then perfusing a cell culture medium whereby the organ is reconstructed.

According to the present invention, the organ can be reconstructed and cultured for long term without separating most of cells which constitute the animal organ.

22 Claims, 19 Drawing Sheets

FIG. II

METHOD OF RECONSTRUCTING ANIMAL ORGANS

FIELD OF THE INVENTION

The present invention relates to a method wherein reconstructed organ is prepared from animal organ and then said reconstructed organ is cultured for a long term. The present invention is useful for evaluation of pharmaceutical effects and toxicity of drugs, cosmetics, chemicals, etc., for development of artificial organs or for preservation of organs to be transplanted, etc.

BACKGROUND OF THE INVENTION

In conducting organ culture of animal organs, fetal (embryo) organs have been mostly used whereby incubation keeping a good survival ratio of cells can be kept during culturing. This is because the organ is small enough and is characterized in being relatively resistant to a state of low oxygen concentration. Incidentally, with regard to organ culture, mature organs of small animals such as rats and mice are classified into those such as ureter, ductus deferens, uterus, trachea, arteries, salivary glands, mammary gland, prostate, seminal vesicle, lung, thyroid, parathyroid, pituitary, pineal, ovary, skin, white adipose tissue, lymph nodes, sympathetic ganglia and eye which can be cultured for around one week if sliced in a thickness of about 2 mm or smaller and those such as brain, liver, thymus, spleen, bone marrow, testis, pancreas, kidney, adrenal gland and spinal ganglion which can be hardly incubated for several days even if sliced in thickness of about 2 mm or smaller [Trowell, O. A.: Exp. Cell Res., 16, 118–147(1959)]. Later than that, a method has been established where liver of mature rats which was believed to be difficult to subject to an organ culture can be cultured for around one week when the organ was sliced into a thickness of about 0.5 mm with a cross section of 1.0–1.5 mm$^2$ and cultured under the condition of 95% $O_2$/5% $CO_2$ [Campbell, A. K. and Hales, C. N.: Exp. Cell Res., 68, 33–42(1971)]. Further after that, a slicer whereby organs can be sliced in a thickness of several hundred micrometers in a precise and quick manner and with minimal trauma has been developed [Krumdieck, C. L., et al.: Analyt. Biochem., 104, 118–123(1980); Smith, P. F., et al.: Life Sci., 36, 1367–1375(1985)]. Nowadays, optimum culturing conditions (buffers for slicing, culture medium, thickness of the slice, shortest culturing time and culturing system for achieving and keeping a good survival ratio of cells, etc.) for sliced organs such as liver, kidney, lung and heart have been established and utilized not only in the field of pharmacology and toxicology but also in many other fields [Parrish, A. R., et al.: Life Sci., 57, 1887–1901 (1995)].

In culturing of organs keeping a good survival ratio of cells, the efficiency of nutrient supply to all inner cells constituting said organ and the efficiency of removal of wastes produced in inner part of the organs are important. In the organs in vivo, those roles are played in a network of capillary vessels. In the conventional organ culture, however, since the network of capillary vessels do not function in an organ culture system, it is necessary to minimize trauma of the excised mature organs and to slice as thin as possible for improving those efficiencies.

If a method whereby mature organ can be cultured in an excised state and a method whereby mature organ can be cultured in a state of somewhat thick slice (several mm to several tens mm) can be established, they will contribute to various medical and pharmaceutical fields such as evaluation of pharmaceutical effects and toxicity of drugs, cosmetics, chemicals, etc., development of artificial organs, preserving organs to be transplanted, etc. However, culturing mature organs (which were believed to be difficult to subject to an organ culture) in an excised state without slicing or culturing those in a state of somewhat thick slice (several mm to several tens mm) has not been conducted at present because it is unable to keep a good survival ratio of cells in the inner area of the culturing organs. Moreover, a problem of trauma which is resulted by a thin slicing of soft organs has been still remaining.

In order to solve the above-mentioned problems, investigations have been made wherein the conventional method for organ culture is completely improved from various viewpoints so that a method for culturing the organ keeping the network of capillary vessels-like structure for easy circulation of the culture medium. It is known that as a method for reconstructing the organ-like structure, in which a network of capillary vessels-like structure is introduced, from cultured cells, a method wherein fibrous root of rice plant or gauze made of cotton is used as a substratum for the circulation for culture medium for animal cells and said animal cells are subjected to a self-assembly and an organoid formation around there (Japanese Published Unexamined Patent Application No. 67626/95 and Japanese Published Unexamined Patent Application No. 298876/95).

SUMMARY OF THE INVENTION

An object of the present invention is to provide a method wherein the animal organ can be cultured in an excised state or in a state of somewhat thick slice (several mm to several tens mm).

The present inventors have conducted investigations wherein a network of capillary vessels kept by animal organs is treated with a cell-dispersible solution to artificially convert to a network of finely cavitized structures and further a reconstruction of the organ to have a network of capillary vessels-like structure by treating the network of finely cavitized structures with cell culture medium, etc. for improving the physical strength of the organ. As the result, they have found a method of organ culture wherein, after perfusion of cell-dispersible solution to the animal organ from vascular system, the animal organ is further perfused with cell culture medium so that the organ is reconstructed and cultured without separating the cells which constitute most of the part of said organ. Thus, the present invention relates to a method of reconstructing the animal organ, which comprises perfusing a cell-dispersible solution in the animal organ from vascular system and then perfusing a cell culture medium and it also relates to a reconstructed organ of the animal organ which is reconstructed by said method.

DETAILED DESCRIPTION OF THE INVENTION

Figure 1:
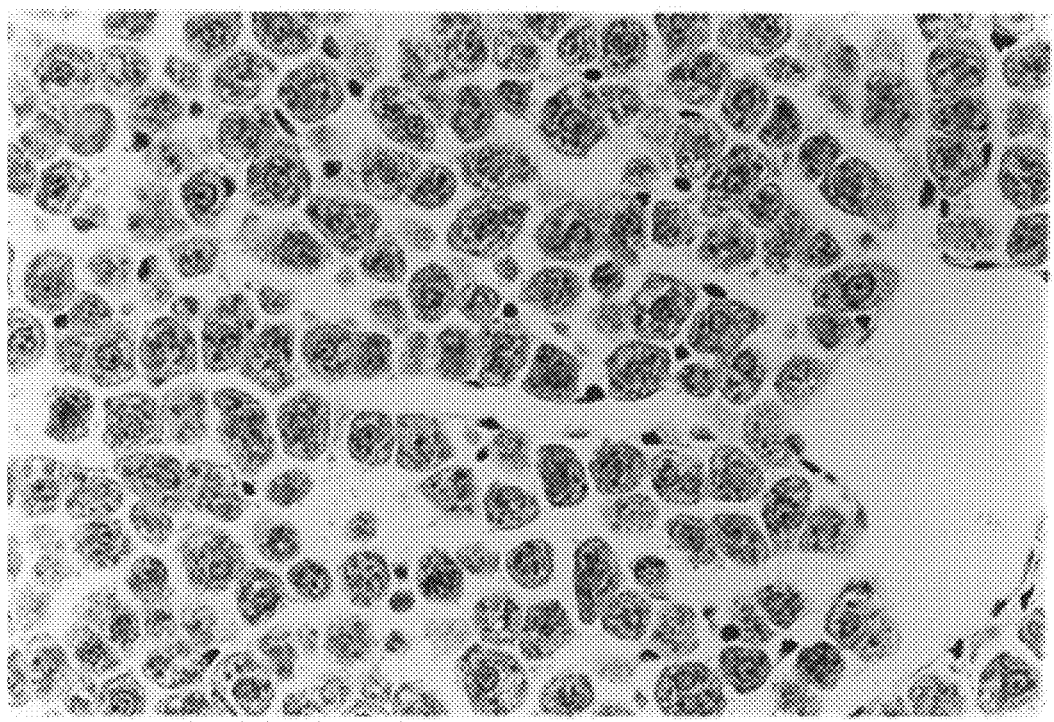
FIG. 1 an optical microscopic photograph of hematoxylin-eosin stained sections of liver which was excised immediately after perfusion of liver digest medium containing collagenase and dispase.
Figure 2:
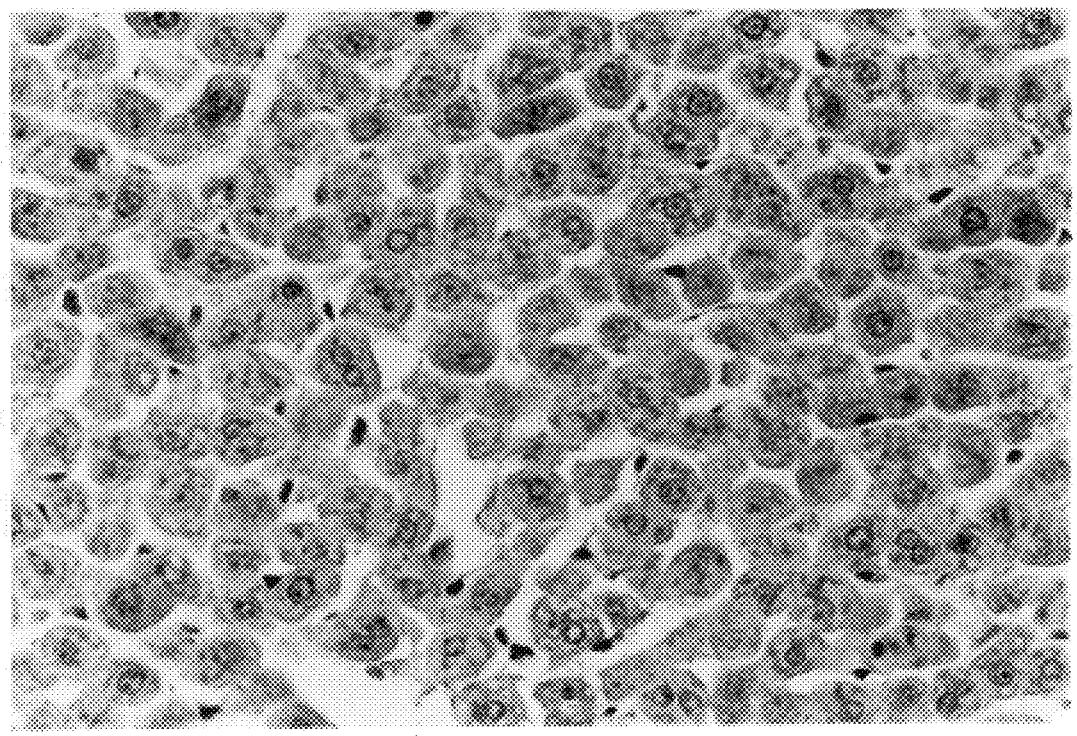
FIG. 2 is an optical microscopic photograph of immunologically type I collagen-stained sections of liver which was excised immediately after perfusion of liver digest medium containing collagenase and dispase.
Figure 3:
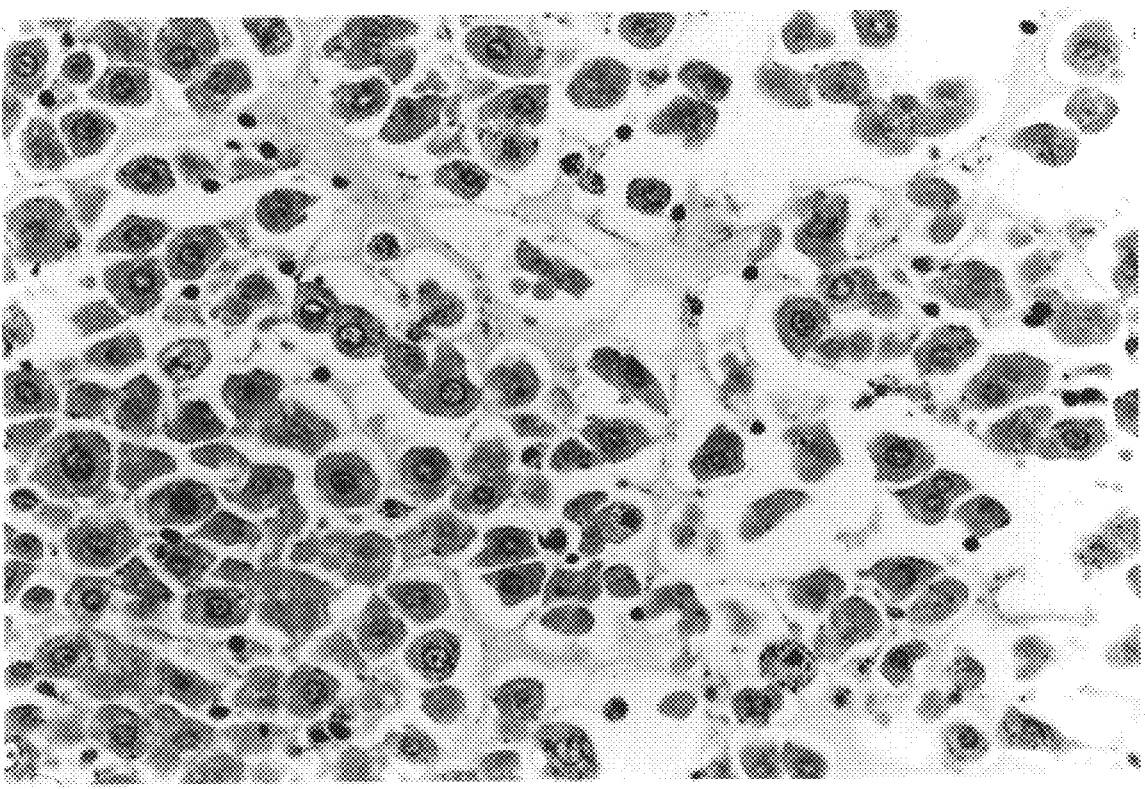
FIG. 3 is an optical microscopic photograph of hematoxylin-eosin stained sections of liver which was excised after perfusion of a homogeneously mixed solution of type I atelocollagen and cell culture medium, and cultured for two hours.
Figure 4:
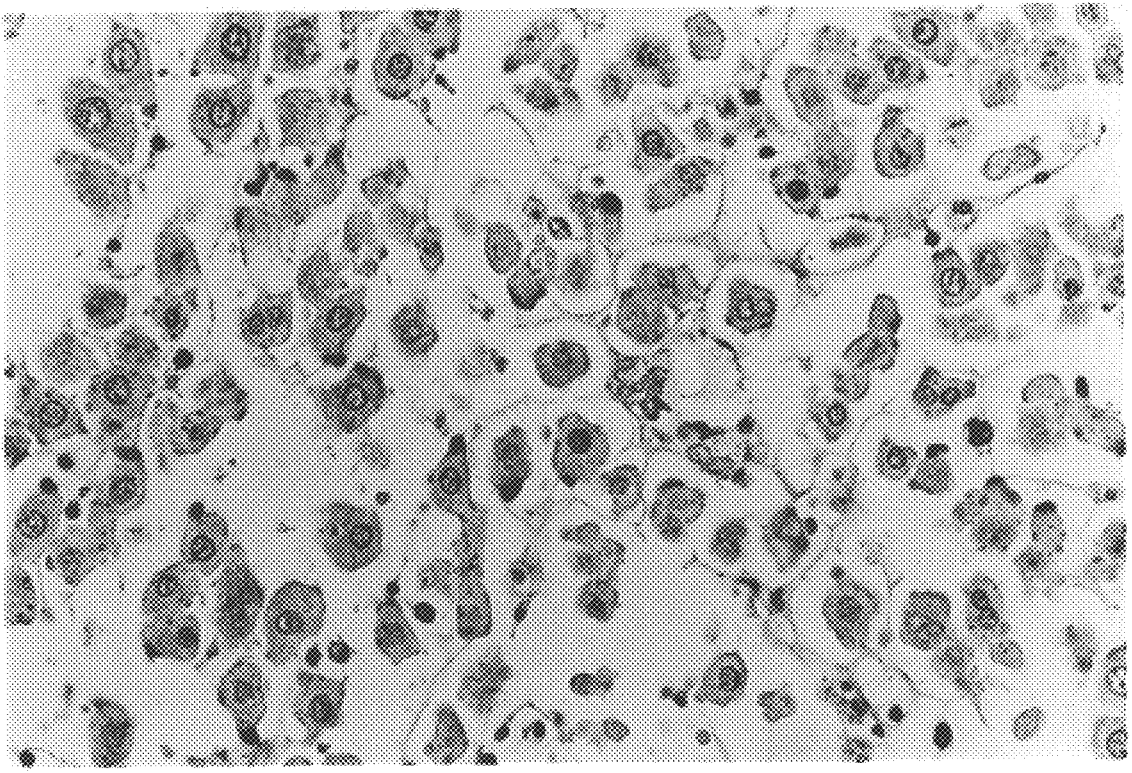
FIG. 4 is an optical microscopic photograph of immunologically type I collagen-stained sections of liver which was excised after perfusion of a homogeneously mixed solution of type I atelocollagen and cell culture medium, and cultured for two hours.

With regard to the animal organ which is used in the present invention, animal organ which is present in living body or previously taken out therefrom can be used. The animal organ, can not be particular limitation so far as it is an organ of mammal such as human, monkey, bovine, sheep, baboon, pig, dog, guinea pig, rat and mouse. For example, there can be used liver, kidney, pancreas, spleen, lung, etc.

With regard to a cell-dispersible solution used in the present invention, any solution can be used so far as it is capable of dispersing the cells. For example, there can be used a solution containing protease, an enzyme capable of decomposing polysaccharides or nucleic acid, or chelate solely or in combination. As a protease, there are, for example, collagenase, trypsin, dispase, elastase, papain and Matrix Metalo Protease (MMP). As depolymerase which is capable of decomposing polysaccharides or nucleic acid are, for example, an enzyme capable of decomposing polysaccharides such as hyaluronidase and an enzyme capable of decomposing nucleic acid such as deoxyribonuclease. As chelating agent, there is no particular limitation so far as it has chelating effect. For example, there can be used EDTA and EGTA. Said cell-dispersible solution can be directly perfused into animal organ. Preferably, the solution can be perfused after a balanced salt solution is perfused to remove blood from the organ. As the balanced salt solution, for example, there can be used Hank's balanced salt solution, phosphate-bufferd saline (PBS) and liver perfusion medium, etc.

It is preferred that the animal used in the present invention is previously administered with an anticoagulant for blood before subjecting to the method of the present invention or that the anticoagulant is previously added to a balanced salt solution and/or cell-dispersible solution so that coagulation of blood is inhibited and cell-dispersible solution and/or balanced salt solution can be easily passed therethrough. With regard to an anticoagulant, anything can be used so far as it is able to prevent coagulation of blood. For example, there can be used heparin, coumarin derivatives, etc.

With regard to the cell culture medium for the present invention, anything can be used so far as it is capable of culturing the animal cells. For example, Dulbecco's modified Eagle medium etc. can be preferably used. When said cell culture medium is perfused, binding of cells to other cells dependent on calcium can be reconstructed. For reconstruction of extracellular matrix, it is preferred that said cell culture medium contains serum and/or extracellular matrix components, for example, collagen, fibronectin, vitronectin, laminin, proteoglycan and glycosaminoglycan. Such serum and/or extracellular matrix components can be derived from the animals of the same species or from those of different species. In addition, it is preferred that said cell culture medium may contain cultured cells derived from animals of same or different species.

Perfusing amount and time of the cell-dispersible solution in accordance with the present invention can be appropriately determined upon the animal organ used. Usually, the perfusion is conducted with a flow rate of 20–35 ml/minute for 5–15 minutes. Perfusing amount and time of the cell medium liquid can be appropriately determined depending upon the organ used. Usually, the perfusion is conducted at a flow rate of 0.5–50 ml/minute, preferably, 1–3 ml/minute for from 20 seconds to three hours, preferably, 5–30 minutes.

The reconstructed organ of the animal organ reconstructed according to a method of the present invention is separated from the living body and said reconstructed organ can be cultured either as it is or after slicing followed by transferring to a culture vessel. Alternatively, after transferring to the culture vessel, said reconstructed organ or slice thereof is embedded and cultured in a hydrogel containing the extracellular matrix components whereby said reconstructed organ or slice thereof can be supported and protected in said hydrogel. As a result, it is possible to effectively culture the reconstructed organ. In said method, the hydrogel can be anything so far as it is able to support or protect said reconstructed organ or slice thereof. For example, there can be used collagen gel, etc.

Detection of morphology and function of the organ which is cultured according to the present invention can be conducted with conventional method. For example, detection can be conducted by hematoxylin-eosin staining, immunostaining using anticollagen antibody, etc.

In accordance with the method of the present invention, it is possible to conduct a reconstruction without separating most of the constituting cells of animal organ and to culture the reconstructed organ for long term.

EXAMPLE 1
Preparation of Reconstructed Organ from Liver of Rats:

SD Rats strain (six weeks old; male; 170–200 g) were lightly anesthetized by whiffing of ether, 0.2 ml of Nembutal (Nembutal injection) was injected intraperitoneally to result in a deeply anesthetized state and then 0.2 ml of heparin [100 units/ml; Heparin injection 1000 manufactured by Novo was diluted to an extent of 10-fold with a phosphate-buffered saline (PBS)] was injected into tail vein. Whole body was disinfected by spraying 70% ethanol for disinfection and the rat was placed on an operating table. Laparotomy was conducted in the order of skin and abdominal muscle using scissors for operation and then intestine was moved to the right-hand side using a sterilized gauze so that portal vein was well exposed. The portal vein was applied with a loop of suture, a break was formed on the portal vein using the pointed head of scissors for ophthalmologic use, and a cannula was quickly inserted to the incised area of the portal vein followed by ligating with a suture together with a treatment that the blood overflowing from the incised area was washed away by a buffer for preperfusion buffer [liver perfusion medium (manufactured by Gibco BRL; catalog number 17701-038) to which 5 units/ml of heparin, 200 units/ml of penicillin and 200 μg/ml of streptomycin were added; the concentrations being final ones] dropping from the pointed head of the cannula. At the same time, inferior vena cava under liver was cut and exsanguination was conducted by perfusing the preperfusion buffer kept at 38° C. for about two minutes with a perister pump at a flow rate of 20 ml/minute. The cut inferior vena cava under the liver was ligated by a clamp and a thoracic cage was cut. Loop of suture was applied to inferior vena cava under diaphragm, a break was formed on the inferior vena cava with a pointed head of scissors for ophthalmologic use, a cannula for harvesting the perfusion buffer was inserted to the incised area and ligation was conducted with suture. Under such a state, a perister pump was operated at a flow rate of 20 ml/minute and a buffer for preperfusion buffer kept at 38° C. was perfused for five minutes. After that, the perfusion medium was changed to a liver digest medium containing collagenase and dispase [Liver Digest Medium (manufactured by Gibco BRL; catalog number 17703-034) to which 1 unit/ml (final concentration) of heparin was added] and this liver digest medium kept at 38° C. was perfused for 11 minutes with a perister pump at a flow rate of 20 ml/minute. Then, the perfusing medium was changed to a 1:9 homogeneously mixed solution of 0.5% type I atelocollagen (Koken Cellgen I-PC; manufactured by Funakoshi; catalog number KO-1115-02) and a cell culture medium (Dulbecco's modified Eagle containing 10% of fetal bovine serum, 20 mM of HEPES, 100 units/ml of penicillin and 10 μg g/ml of streptomycin), and said homogeneously mixed solution (final concentration of type I atelocollagen being 0.05%) cooled at 4° C. was perfused for ten minutes under operation of aperister pump at a flow rate of 2 ml/minute. After that, the perfusion medium was further changed to a 1:1 homogeneously mixed solution of 0.5% type I atherocollagen and the cell culture medium and said homogeneously mixed solution (final concentration of type I atherocollagen being 0.25%) cooled at 4° C. was perfused for ten minutes with a perister pump at a flow rate of 2 ml/minute. Ligation by suture was conducted at the site of the area of portal vein and inferior vena cava to the direction of liver and, after detaching each cannula, liver was excised together with a part of diaphragm and ligated sites of portal vein and inferior vena cava. The excised liver was washed twice with 40 ml of the cell culture medium poured into a culture dish having a diameter of 10 cm, transferred to another culture dish to which 40 ml of fresh cell culture medium was poured and culturing was conducted for two hours in a moisturized incubator at 37° C. under 5.0% of $CO_2$ and 95% of air so that the perfused collagen was completely gelled. Each of the liver excised immediately after perfusion of the liver digest medium containing collagenase and dispase and the liver which was excised after perfusion of a homogeneously mixed solution of type I atherocollagen and cell culture medium and cultured for two hours was fixed with a 10% formalin neutral buffer solution, dehydrated by a conventional method and embedded in paraffin, slice having a thickness of 4 μm was prepared near the center of the lobe of liver, and a hematoxylin-eosin staining and an immunostaining with anti-type I collagen antibody (manufactured by Cosmo Bio; catalog number LB-1197) were conducted. As a result , it has been ascertained by observation under an optical microscope that, although a network of finely cavitated structures was formed in the liver which was excised immediately after perfusion with the liver digest medium containing collagenase and dispase, most of the liver-constituting cells were present without being separated and the immunostaining of anti-type I collagen antibody was negative and that, in the liver which was excised after perfusion with a homogeneously mixed solution of type I atelocollagen and cell culture medium followed by culturing for two hours, immunostaining of the anti-type I collagen antibody was positive and the network of finely cavitated structures formed therein was filled with extrinsic gelled collagen (cf. FIG. 1 to FIG. 4).

Figure 5:
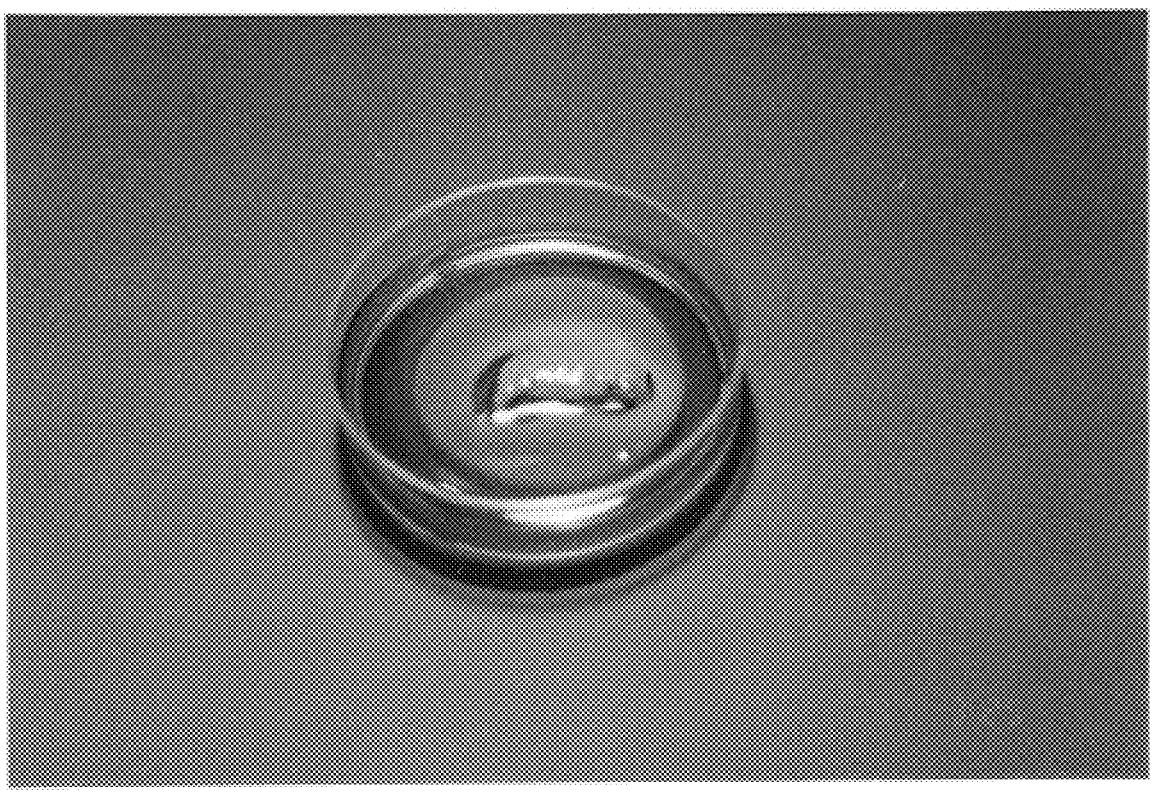
FIG. 5 is a photograph picture of the collagen gel in which a lobe of the reconstructed liver by the present invention was embedded and was cultured for two weeks in a culture dish having a diameter of 6 cm.
Figure 6:
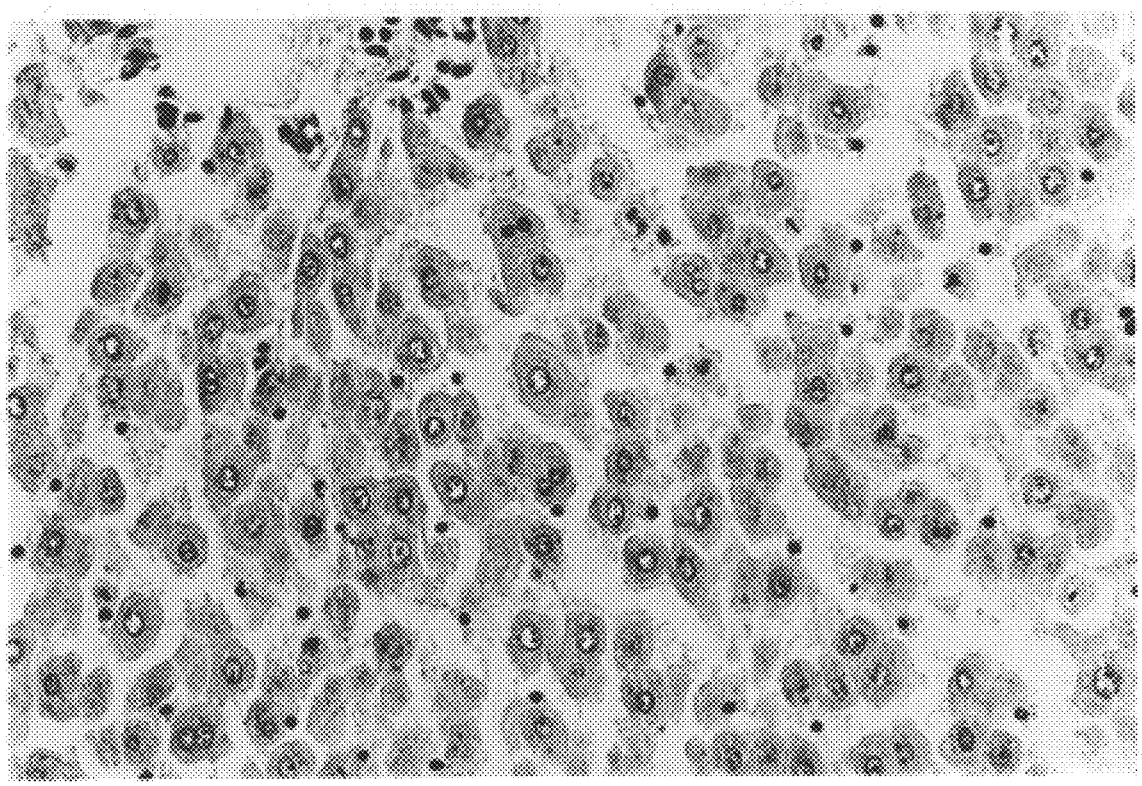
FIG. 6 is an optical microscopic photograph of hematoxylin-eosin stained sections of a lobe of the reconstructed liver by the present invention which was embedded in collagen and cultured for one day.
Figure 7:
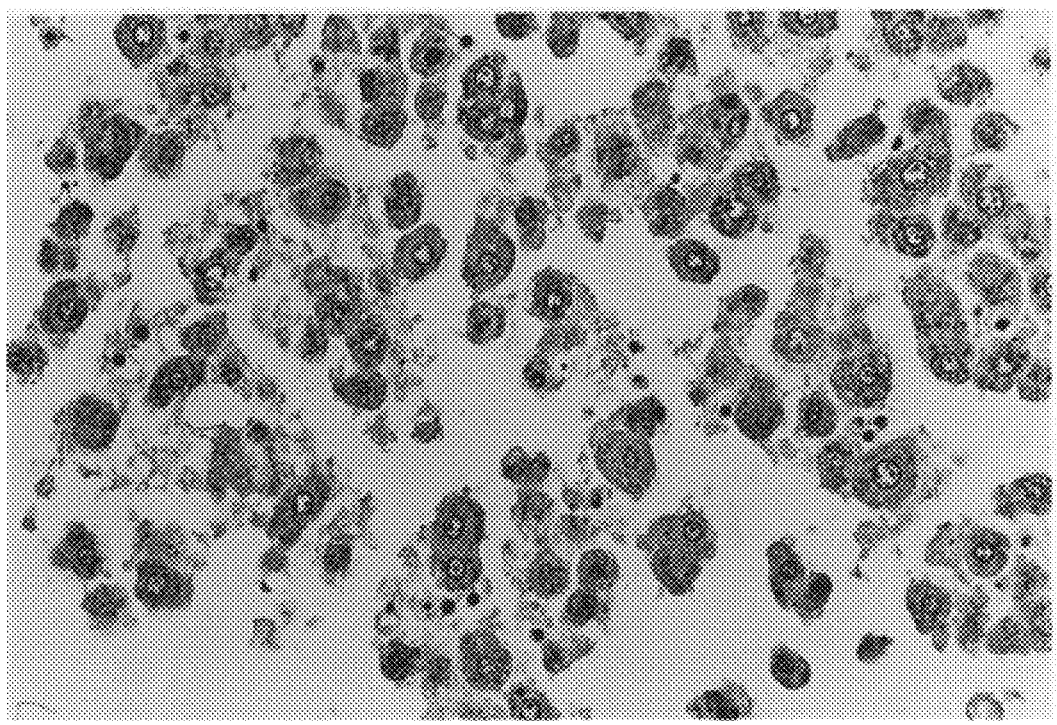
FIG. 7 is an optical microscopic photograph of immunologically type I collagen-stained sections of a lobe of the reconstructed liver by the present invention which was embedded in collagen and cultured for one day.
Figure 8:
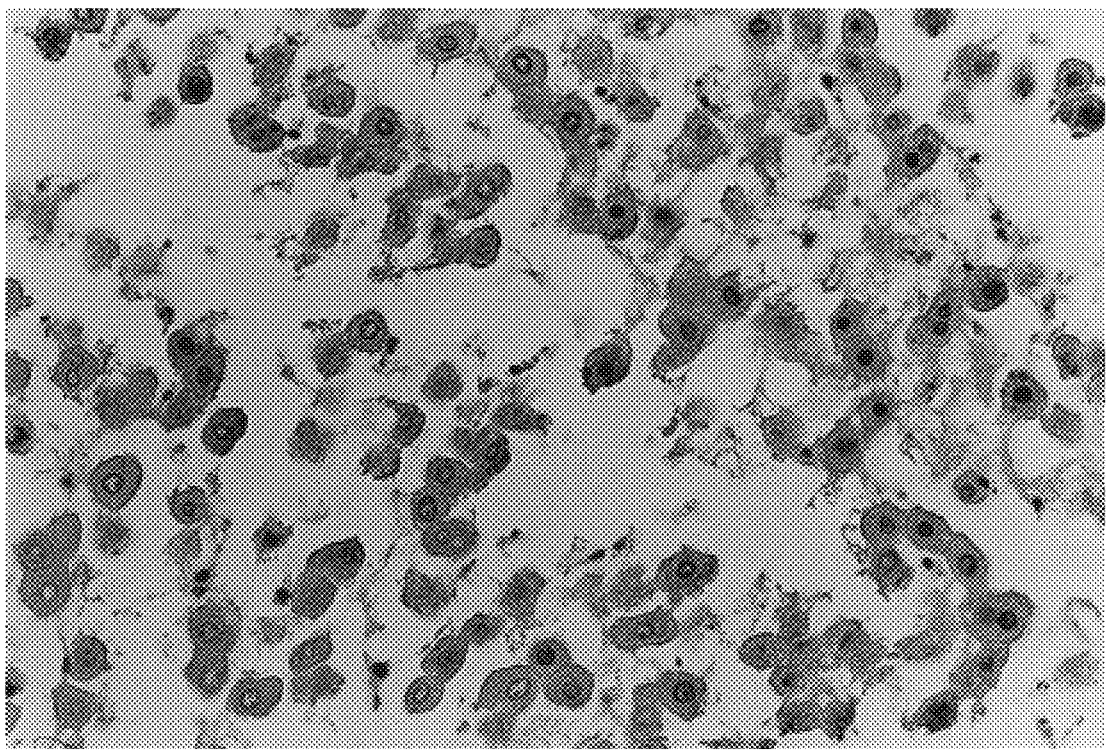
FIG. 8 is an optical microscopic photograph of hematoxylin-eosin stained sections of a lobe of the reconstructed liver by the present invention which was embedded in collagen and cultured for one week.
Figure 9:
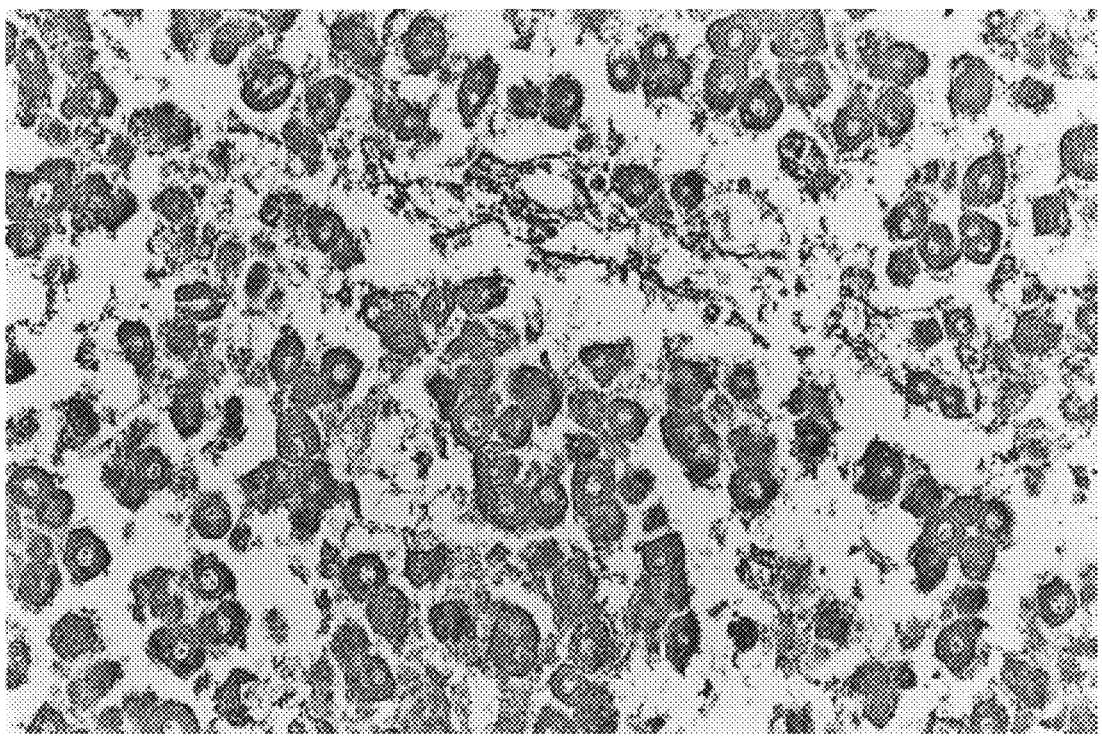
FIG. 9 is an optical microscopic photograph of immunologically type I collagen-stained sections of a lobe of the reconstructed liver by the present invention which was embedded in collagen and cultured for one week.
Figure 10:
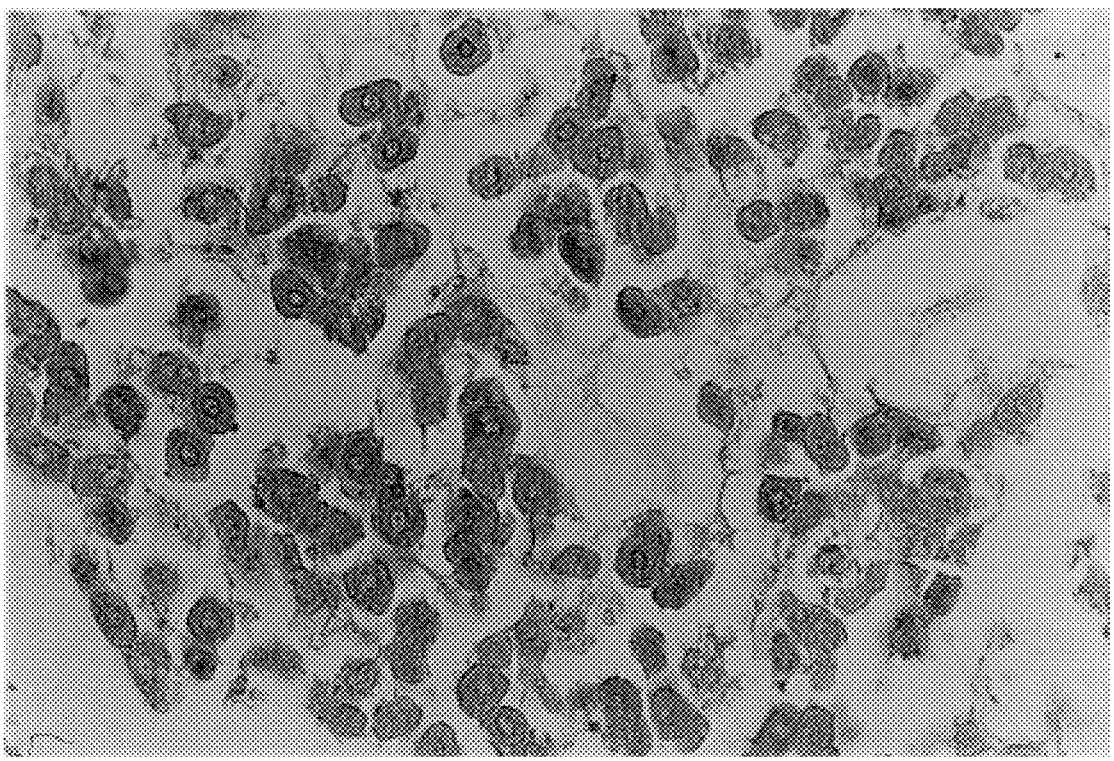
FIG. 10 is an optical microscopic photograph of hematoxylin-eosin stained sections of a lobe of the reconstructed liver by the present invention which was embedded in collagen and cultured for two weeks.
Figure 11:
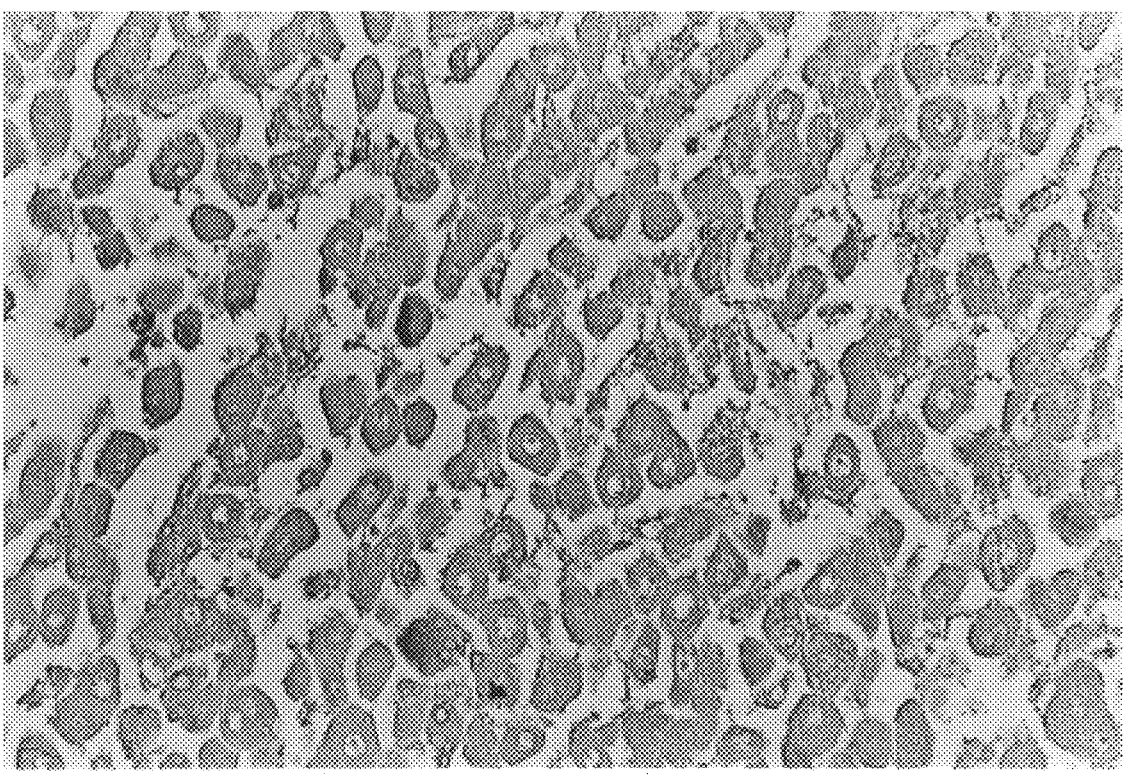
FIG. 11 is an optical microscopic photograph of immunologically type I collagen-stained sections of a lobe of the reconstructed liver by the present invention which was embedded in collagen and cultured for two weeks.
Figure 12:
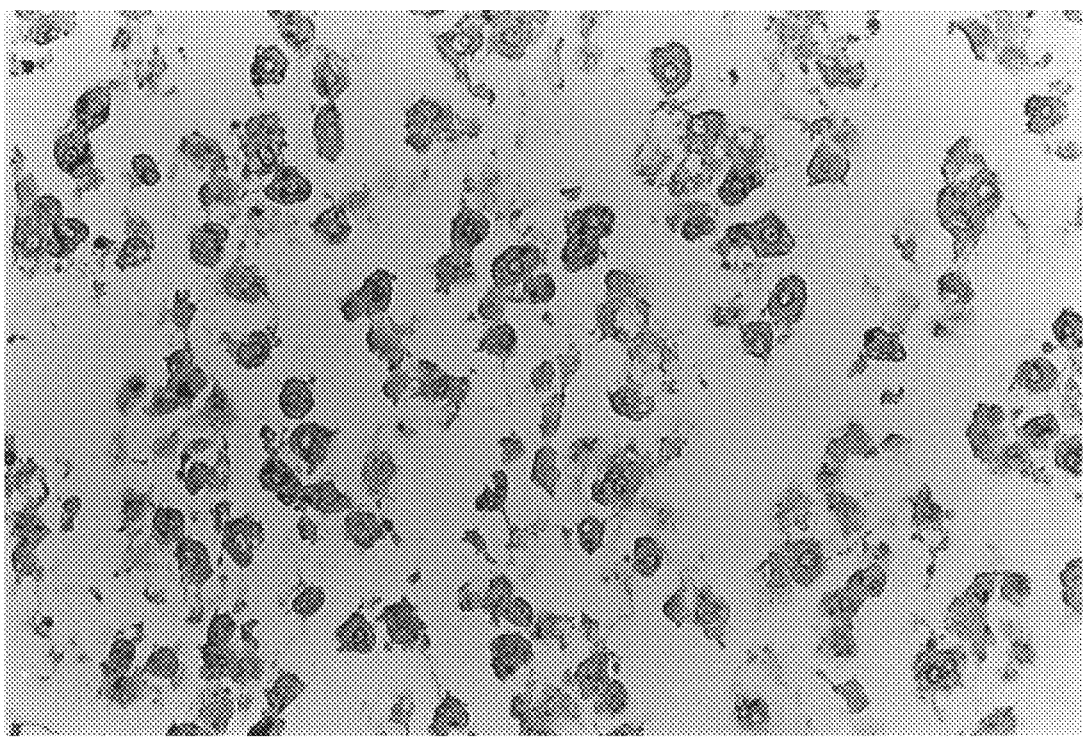
FIG. 12 is an optical microscopic photograph of hematoxylin-eosin stained sections of a lobe of the reconstructed liver by the present invention which was embedded in collagen and cultured for three weeks.
Figure 13:
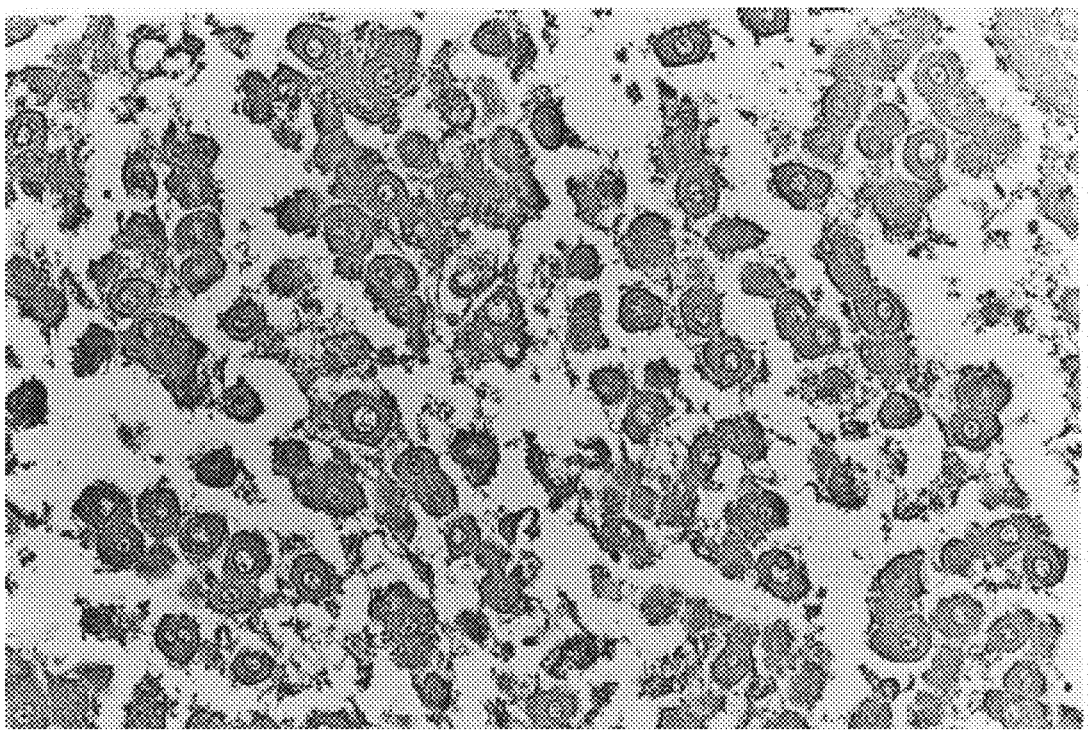
FIG. 13 is an optical microscopic photograph of immunologically type I collagen-stained sections of a lobe of the reconstructed liver by the present invention which was embedded in collagen and cultured for three weeks.
Figure 14:
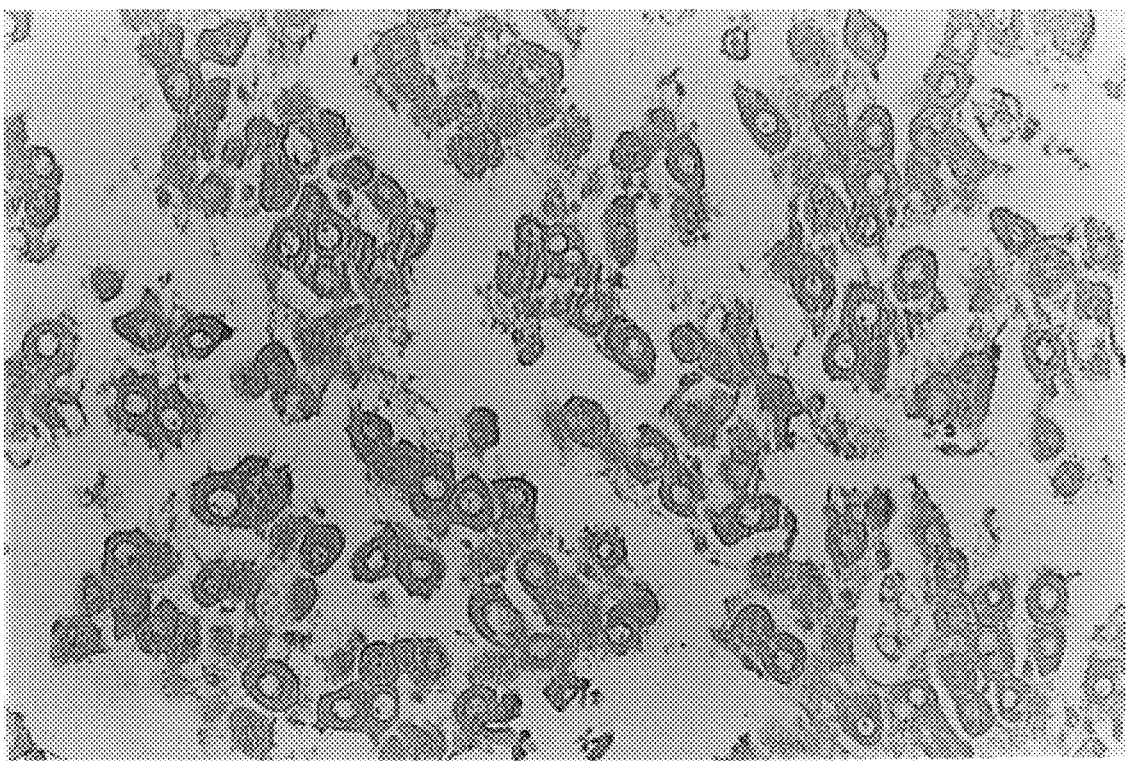
FIG. 14 is an optical microscopic photograph of hematoxylin-eosin stained sections of a lobe of the reconstructed liver by the present invention which was embedded in collagen and cultured for one month.
Figure 15:
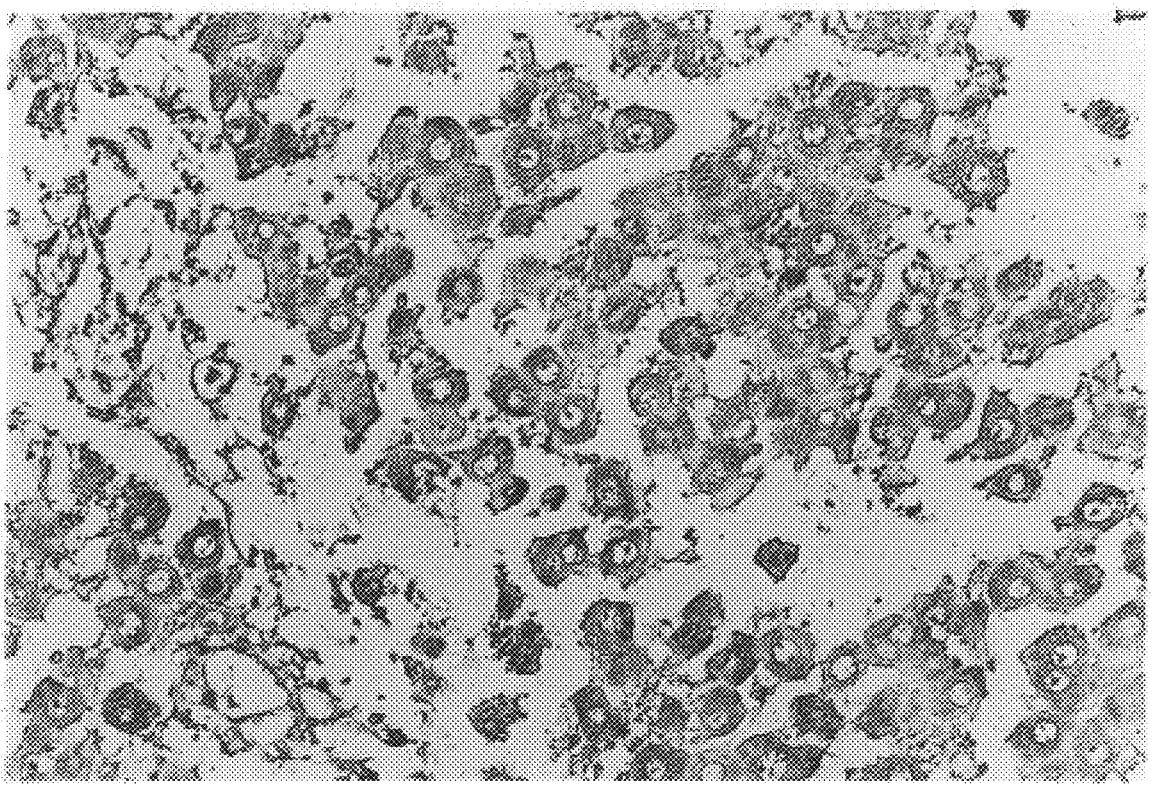
FIG. 15 is an optical microscopic photograph of immunologically type I collagen-stained sections of a lobe of the reconstructed liver by the present invention which was embedded in collagen and cultured for one month.

EXAMPLE 2
Culturing of Reconstructed Organ Prepared from Rat Liver:

The reconstructed liver obtained in Example 1 which was perfused with a homogeneously mixed solution of type I atelocollagen and cell culture medium excised and cultured for two hours was treated with scissors for operation to remove diaphragm, portal vein and inferior vena cava attached thereto and then separated into lobes using scissors for operation. Each of the separated lobes was placed on 2 ml of 0.25% type I collagen gel which was previously prepared in a culture dish having a diameter of 35 mm (manufactured by Falcon; catalog number 1008), then 2–5 ml of 0.25% type I collagen solution was poured thereon to cover the lobe and cultured for one day in a moisturized incubator at 37° C. under 5.0% of $CO_2$ and 95% of air so that the lobe was embedded in the collagen gel. The collagen gel in which the lobe of the reconstructed liver was embedded was taken out, transferred into a culture dish having a diameter of 6 cm (manufactured by Falcon; catalog number 1007) and cultured in a moisturized incubator at 37° C. under 5.0% of $CO_2$ and 95% of air (FIG. 5). The cell culture medium was changed every other day. Each lobe of the reconstructed liver which was embedded in collagen gel and cultured for one day, one week, two weeks, three weeks and one month, was fixed with 10% formalin neutral buffer solution, dehydrated by a conventional method and embedded in paraffin and slices with a thickness of 4 μm were prepared near the center of the lobe and subjected to a hematoxylin-eosin staining and to an immunostaining with anti-collagen type I antibody. As a result, it was ascertained by an optical microscopic observation that, from the first day to even after culturing for one month, many histologically healthy cells were observed inside of the each lobe of reconstructed liver and that the immunostaining with the collagen type I was positive around the cells and there were full of the extrinsic gelled collagen (See FIG. 6 to FIG. 15). Incidentally, the above 0.25% type I collagen gel was prepared bycompletely gellinga 1:1 homogeneously mixed solution of 0.5% type I collagen (Koken Cellgen I-AC; manufactured by Funakoshi, catalog number KO-1115-00) and a cell culture medium in a moisturized incubator at 37° C. for not shorter than 30 minutes under 5.0% of $CO_2$ and 95% of air.

EXAMPLE 3
Introduction of Extrinsic Cells into the Organ Reconstructed from Rat Liver:

SD Rats strain (seven weeks old; male; 170–200 g) were lightly anesthetized by whiffing of ether, 0.2 ml of Nembutal (Nembutal injection) was injected intraperitoneally to result in a deeply anesthetized state and then 0.2 ml of heparin [100 units/ml; Heparin injection 1000 manufactured by Novo was diluted to 10-fold with a PBS] was injected into tail vein. Whole body was disinfected by spraying 70% ethanol for disinfection and the rat was placed on an operating table. Laparotomy was conducted in the order of skin and abdominal muscle using scissors for operation and then intestine was moved to the right-hand side using a sterilized gauze immersed with ethanol for disinfection so that portal vein was well exposed. The portal vein was applied with a loop of suture, a break was formed on the portal vein using the pointed head of scissors for ophthalmologic use, and a cannula was quickly inserted to the incised area of the portal vein followed by ligating with a suture together with a treatment that the blood overflowing from the incised area was washed away by a buffer for preperfusion buffer [liver perfusion medium (manufactured by Gibco BRL; catalog number 17701-038) to which 5 units/ml of heparin, 200 units/ml of penicillin and 200 μg/ml of streptomycin were added; the concentrations being final ones] dropping from the pointed head of the cannula. At the same time, inferior vena cava under liver was cut and exsanguination was conducted by perfusing the buffer for preperfusion buffer, kept at 38° C. for about two minutes with a perister pump at a flow rate of 20 ml/minute. The cut inferior vena cava under the liver was ligated by a clamp and a thoracic cage was cut. Loop of suture was applied to inferior vena cava under diaphragm, a break was formed on the inferior vena cava with a pointed head of scissors for ophthalmologic use, a cannula for harvesting the perfusion medium was inserted to the incised area and ligation was conducted with suture. Under such a state, a perister pump was operated at a flow rate of 20 ml/minute and a preperfusion buffer, kept at 38° C. was perfused for five minutes. After that, the perfusion medium was changed to a liver digest medium containing collagenase and dispase [Liver Digest Medium (manufactured by Gibco BRL; catalog number 17703-034) to which 1 unit/ml (final concentration) of heparin was added] and this liver digest medium kept at 38° C. was perfused for 11 minutes with a perister pump at a flow rate of 20 ml/minute. Then, a cell culture medium (Dulbecco's modified Eagle medium containing 10% of fetal bovine serum, 20 mM of HEPES, 100 units/ml of penicillin and 100 μg/ml of streptomycin) wherein about $1 \times 10^5$ cells/ml of human dermal fibroblasts fluorescently labeled with 2 μM of calcein AM (Live/Dead Viability/Cytotoxicity Kit; manufactured by Molecular Probes; catalog number L-3224) for about 30 minutes was suspended was perfused for five minutes with a perister pump at a flow rate of 20 ml/minute. Ligation by suture was conducted at the site of the area of portal vein and inferior vena cava to the direction of liver and, after detaching each cannula, liver was excised together with a part of diaphragm and ligated sites of portal vein and inferior vena cava. The excised liver was washed twice with 40 ml of the cell culture medium poured into a culture dish having a diameter of 10 cm, transferred to another culture dish to which 40 ml of fresh cell culture medium was poured and culturing was conducted for about three hours in a moisturized incubator at 37° C. under 5.0% of $CO_2$ and 95% of air. The liver obtained hereinabove, which was perfused with human dermal fibroblasts fluorescently labeled with calcein AM, was washed with a sufficient amount of phosphate-buffered saline (PBS) and was observed under an inverted fluorescent microscope. As a result, it was ascertained that the human dermal fibroblasts fluorescently labeled with calcein AM were introduced and distributed into the reconstructed lobe of liver.

Figure 16:
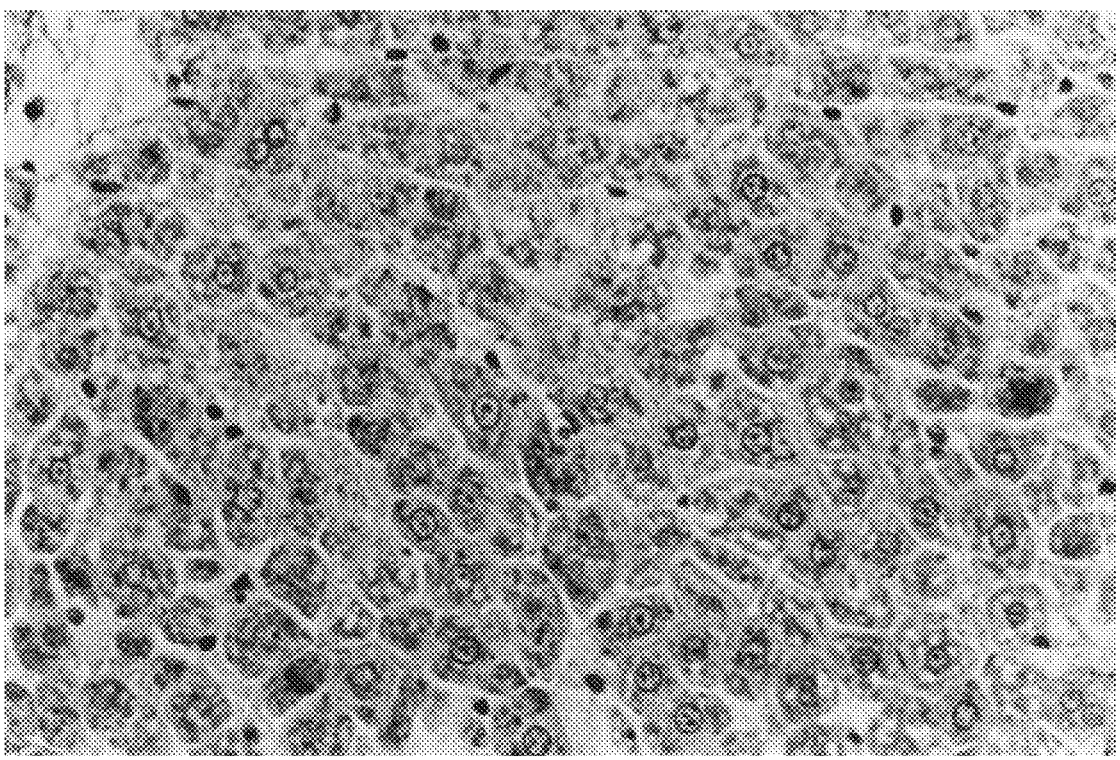
FIG. 16 is an optical microscopic photograph of hematoxylin-eosin stained sections of a two hours-cultured lobe of exsanguinated liver.
Figure 17:
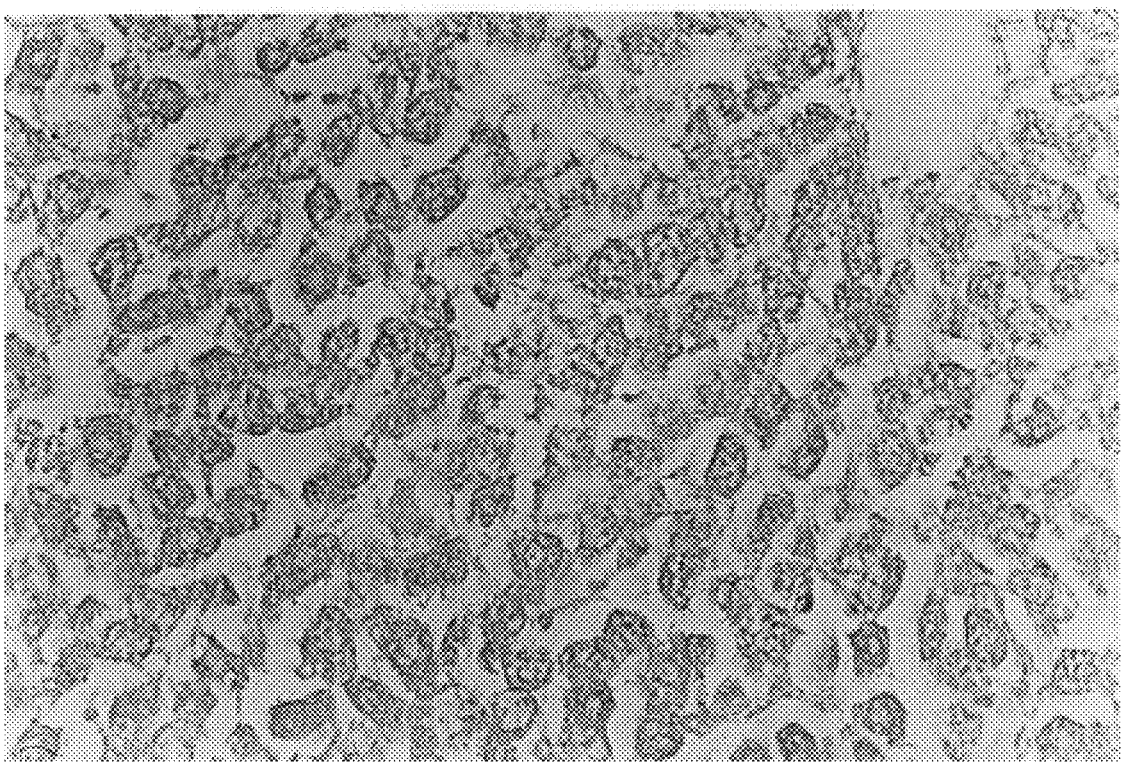
FIG. 17 is an optical microscopic photograph of hematoxylin-eosin stained sections of a three days-cultured lobe of exsanguinated liver.

REFERENCE EXAMPLE 1
Organ Culture of Exsanguinated Rat Liver:

The liver obtained in Example 1 which was excised immediately after perfusion with a preperfusion buffer was Cultured for two hours, then diaphragm, portal vein and inferior vena cava attached thereto were detached by scissors for operation. After that, it was separated into each lobe using the scissors for operation. Each of the separated lobes was transferred to a culture dish having a diameter of 6 cm (manufactured by Falcon; catalog number 1007) in which 10 ml of fresh cell culture medium was poured and then cultured in a moisturized incubator at 37° C. under 5.0% of $CO_2$ and 95% of air. The cell culture medium was changed every day. After culturing for two hours and three days, each lobe of the liver was fixed with 10% formalin neutral buffer solution dehydrated by a conventional method and embedded in paraffin and slices with a thickness of 4 μm were prepared near the center of the lobe and subjected to a hematoxylin-eosin staining. As a result, it was ascertained by an optical microscopic observation that, in the liver lobe cultured for two hours, no erythrocyte was observed because of sufficient exsanguination, and cells constituting the liver were histomorphologically healthy, while in the liver lobe cultured for three days, most of the liver-constituting cells were histomorphologically necrotic (See FIG. 16 and FIG. 17).

Figure 18:
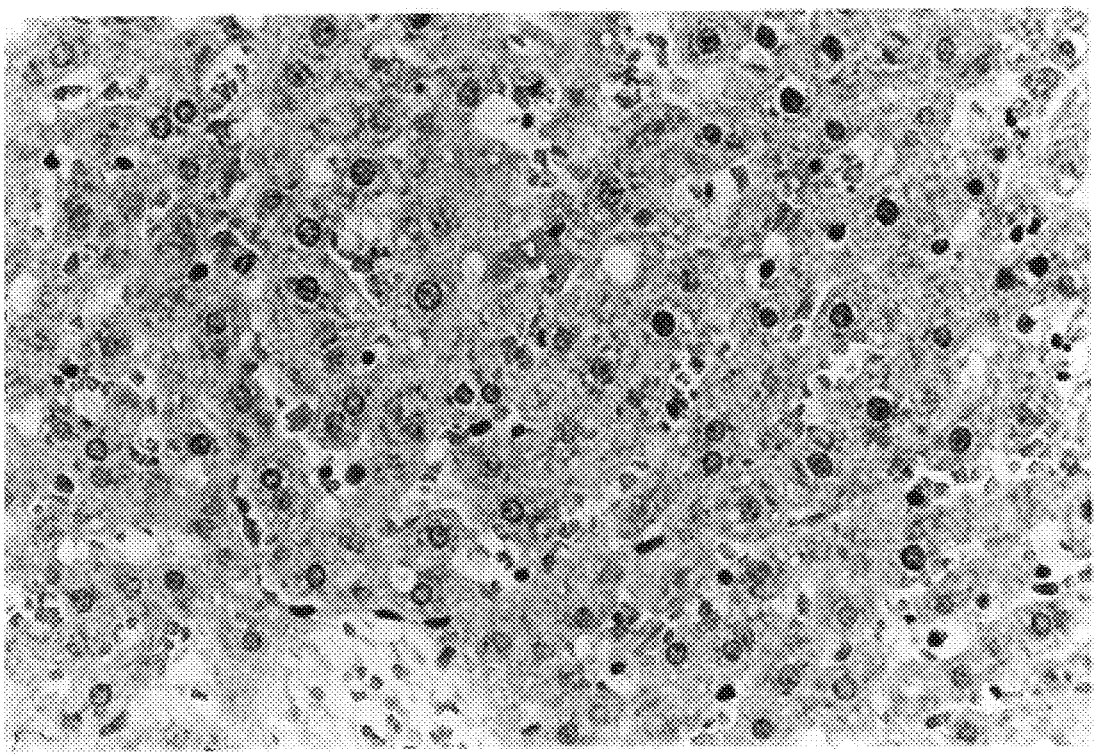
FIG. 18 is an optical microscopic photograph of hematoxylin-eosin stained sections of a two hours-cultured lobe of untreated liver.
Figure 19:
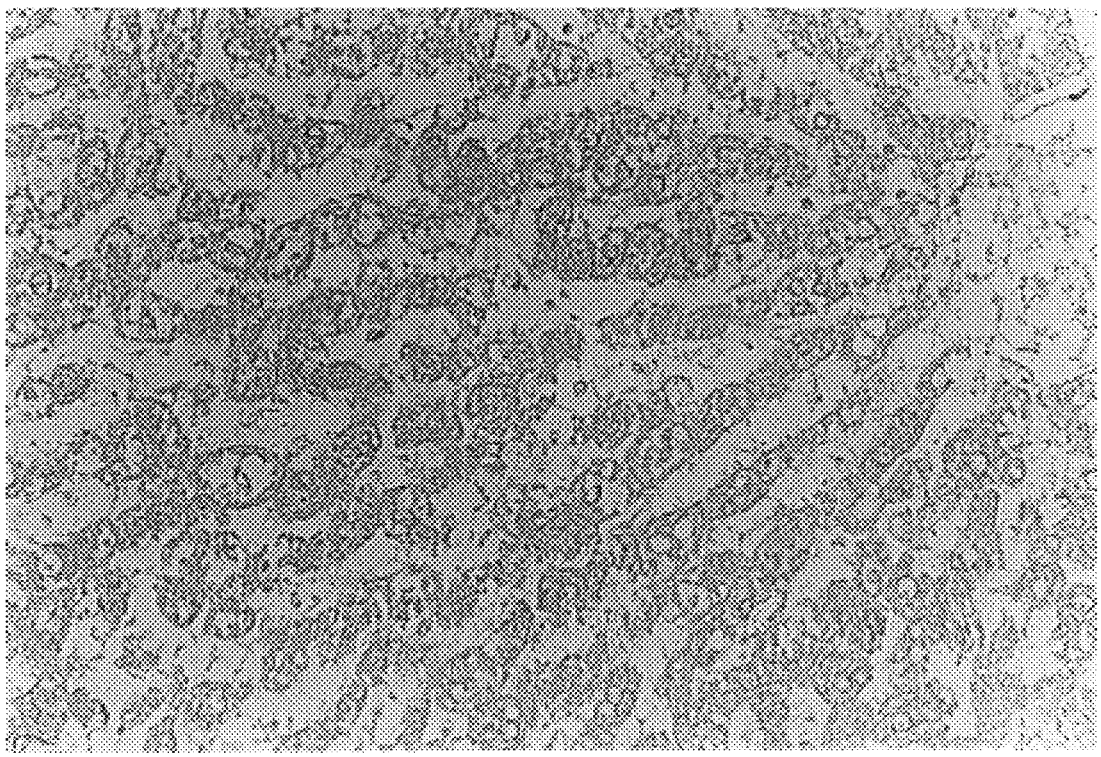
FIG. 19 an optical microscopic photograph of hematoxylin-eosin stained sections of a three days-cultured lobe of untreated liver.

REFERENCE EXAMPLE 2
Organ Culture of Untreated Rat Liver:

Rats Rats (six weeks old; male; 170–200 g) were lightly anesthetized by whiffing of ether and 0.2 ml of Nembutal was injected intraperitoneally to result in a deeply anesthetized state. Whole body was disinfected by spraying 70% ethanol for disinfection and the rat was placed on an operating table. Laparotomy was conducted in the order of skin and abdominal muscle using scissors for operation and then intestine was moved to the right-hand side using a sterilized gauze so that portal vein was well exposed. After that, thorax was opened. Portal vein and inferior vena cava were ligated with a loop of suture. After allowing to stand in that state for 10 minutes, the liver was excised with a part of diaphragm and ligated sites of portal vein and inferior vena cava. The excised liver was cultured for two hours, then diaphragm, portal vein and inferior vena cava attached thereto were detached by scissors for operation. After that, it was separated into lobes using the scissors for operation. Each of the separated lobes was transferred to a culture dish having a diameter of 6 cm (manufactured by Falcon; catalog number 1007) in which 10 ml of fresh cell culture medium was poured and then cultured in a moisturized incubator at 37° C. under 5.0% of $CO_2$ and 95% of air. The cell culture medium was changed every day. After culturing for two hours and three days, each lobe of the liver was fixed with 10% formalin neutral buffer solution, dehydrated by a conventional method and embedded in paraffin and slices with a thickness of 4 $\mu$m were prepared near the center of the lobe and subjected to a hematoxylin-eosin staining. As a result, it was ascertained by an optical microscopic observation that, in the liver lobe after culturing for two hours, central vein and sinusoid cavity where erythrocytes were present were observed and the liver-constituting cells were histomorphologically healthy and that, in the liver lobe after culturing for three days, most of the liver-constituting cells were histomorphologically necrotic (See FIG. 18 and FIG. 19).

What is claimed is:

1. A method of reconstructing an animal organ comprising: perfusing the organ throuah its vascular system with a solution comprising a cell-dispersing agent for an amount of time sufficient to create a network of cavitized structures; perfusing the organ through its vascular system with a solution of a cell culture medium and a substance selected from the group consisting of serum, an extracellular matrix component and cultured cells; and culturing the organ or at least a slice of the organ.

2. The method according to claim 1 wherein the animal is mammal.

3. The method according to claim 1, wherein the animal is human.

4. The method according to claim 1, wherein the animal is mammal except human.

5. The method of culturing the reconstructed organ which comprises separating the animal organ reconstructed by a method of claim 1 from living body, transferring said reconstructed organ as it is or after being sliced to culture vessel and culturing.

6. The method according to claim 1 wherein the animal organ is in living body.

7. The method according to claim 1, wherein the animal organ is previously taken out of the living body.

8. The method according to claim 1 wherein the animal organ is liver, kidney, pancreas, spleen or lung.

9. The method according to claim 1 wherein the cell-dispersing agent is at least one substance selected from the group consisting of protease, enzyme which is capable of decomposing polysaccharides, enzyme which is capable of decomposing nucleic acid, and chelating agent.

10. The method of claim 9 wherein the cell-dispersing agent is at least one protease selected from the group consisting of collagenase, trypsin, dispase, elastase, papain and matrix metalo protease.

11. The method according to claim 9 wherein the cell-dispersing agent is at least one enzyme selected from the group consisting of hyaluronidase and deoxyribonuclease.

12. The method according to claim 9 wherein the cell-dispersing agent is at least one chelating agent selected from the group consisting of EDTA and EGTA.

13. The method according to claim 1 wherein perfusing a balanced salt solution before perfusing a cell-dispersing solution whereby blood is removed from the organ.

14. The method according to claim 1 wherein the animal is previously administered anticoagulant for blood.

15. The method according to claim 14 wherein the anticoagulant for blood is added to at least one substance selected from the group consisting of a balanced salt solution and a cell-dispersing solution.

16. The method according to claim 1 wherein the cell culture medium contains at least one selected from the group consisting of serum and extracellular matrix component.

17. The method according to claim 16 wherein the extracellular matrix component is collagen.

18. The method according to claim 16 wherein the serum or the extracellular matrix component is derived from the animal of the same or different species.

19. The method according to claim 16 wherein the cell culture medium contains the cultured cells derived from animal of the same or different species.

20. A method of culturing a reconstructed organ, which comprises separating an animal organ reconstructed by the method according to claim 1 from a living body; transferring said entire reconstructed organ or said reconstructed organ after being sliced, to a culturing vessel; embedding said entire reconstructed organ or said reconstructed organ after being sliced in hydrogel containing extracellular matrix components; and culturing said entire reconstructed organ or said reconstructed organ after being sliced.

21. The method of claim 20 wherein the hydrogel is collagen gel.

22. The reconstructed organ of the animal organ which is reconstructed by a method according to any one of claims 1 to 21.

* * * * *